(12) United States Patent
Chesson

(10) Patent No.: US 8,961,050 B2
(45) Date of Patent: Feb. 24, 2015

(54) FILTERED FLUID PUMP DISPENSER WITH DIRECT APPLICATION MODE

(75) Inventor: Jerry S. Chesson, Durham, NC (US)

(73) Assignee: RMI Polymers, Inc., Durham, NC (US)

( * ) Notice: Subject to any disclaimer, the term of this patent is extended or adjusted under 35 U.S.C. 154(b) by 956 days.

(21) Appl. No.: 12/580,090

(22) Filed: Oct. 15, 2009

(65) Prior Publication Data

US 2011/0092868 A1 Apr. 21, 2011

(51) Int. Cl.
| | |
|---|---|
| B43K 5/02 | (2006.01) |
| A61F 13/40 | (2006.01) |
| A45D 34/04 | (2006.01) |
| B05B 11/00 | (2006.01) |
| B05B 15/00 | (2006.01) |
| A45D 34/02 | (2006.01) |

(52) U.S. Cl.
CPC ........... A61M 35/006 (2013.01); A45D 34/045 (2013.01); B05B 11/3047 (2013.01); B05B 15/005 (2013.01); B05B 15/008 (2013.01); A45D 34/02 (2013.01); A45D 2200/057 (2013.01); A45D 2200/1018 (2013.01)
USPC ........... 401/188 R; 401/118; 401/38; 604/290

(58) Field of Classification Search
CPC .................................................... B05B 15/008
USPC ................ 401/188 R, 195, 207, 27, 38, 118; 222/189.1, 189.06, 382; 604/1, 290
See application file for complete search history.

(56) References Cited

U.S. PATENT DOCUMENTS

| | | | | |
|---|---|---|---|---|
| 2,043,678 | A * | 6/1936 | Schmalz | 604/1 |
| 3,146,806 | A * | 9/1964 | Ginsburg | 401/122 |
| 4,220,285 | A * | 9/1980 | Gualdi | 222/383.1 |
| 4,273,272 | A * | 6/1981 | Blanc | 222/464.4 |
| 4,301,799 | A * | 11/1981 | Pope et al. | 222/189.1 |
| 5,103,812 | A * | 4/1992 | Salamone et al. | 602/52 |
| 5,195,664 | A * | 3/1993 | Rhea | 222/382 |
| 5,516,505 | A * | 5/1996 | McDow | 604/290 |
| 6,142,384 | A * | 11/2000 | Shafik | 222/189.1 |
| 6,250,508 | B1 * | 6/2001 | Geser et al. | 222/189.1 |
| 6,833,072 | B1 * | 12/2004 | Krestine et al. | 222/189.1 |
| 7,661,563 | B2 * | 2/2010 | De Lataulade | 222/382 |
| 2006/0131337 | A1 * | 6/2006 | Mertins | 222/164 |
| 2007/0023544 | A1 * | 2/2007 | Woods | 239/302 |
| 2011/0248052 | A1 * | 10/2011 | Kelly et al. | 222/382 |
| 2013/0294809 | A1 * | 11/2013 | Eggers et al. | 401/188 R |

* cited by examiner

Primary Examiner — David Walczak
Assistant Examiner — Bradley Oliver
(74) Attorney, Agent, or Firm — Coats & Bennett, PLLC

(57) ABSTRACT

A filtered fluid pump spray dispenser and applicator assembly includes a container having a pump spray mechanism connected to a fluid feed tube immersed in a fluid to be dispensed. The open end of the fluid feed tube is covered by a porous and permeable filter, which filters particulate matter from the fluid during spray mode fluid dispensing. The pump mechanism and fluid feed tube may be removed, and fluid contained in the filter applied directly to a surface in direct application mode fluid dispensing.

5 Claims, 3 Drawing Sheets

100
FILTERED FLUID PUMP DISPENSER WITH DIRECT APPLICATION MODE

TECHNICAL FIELD

The present invention relates generally to pump spray bottles, and in particular to a pump spray bottle having a fluid filter that additionally acts as a fluid applicator.

BACKGROUND

The dispensing of fluid from a container by manual actuation of a pump or similar mechanism is well known in the art. For example, fluids such as perfume, insect repellent, and antibiotics are commonly packaged and sold in glass or plastic containers having an integral, manually actuated pumping mechanism for applying the fluid to a relatively large area of skin. The pumping mechanism may comprise an air bladder, commonly used to dispense perfume, or a pump mechanism operative to draw, atomize, and spray fluid upon being manually depressed. The latter type of pump mechanism is typically integrally formed with a cap that seals the fluid within the bottle. A fluid feed tube connects to the pumping mechanism, and extends within the bottle, immersing an open end in the fluid to be dispensed. One known problem with prior art pump spray bottles is that particulate matter which may be in the bottle, whether suspended in the fluid or settled at the base of the bottle, may be drawn into the fluid feed tube and clog the spray mechanism.

While pump spray bottles are effective for applying fluid to a relatively large surface area, in many cases a more controlled application of the fluid to a surface is desired. Many applicators to achieve this are known in the art. For example, fingernail paint is typically dispensed in a container having a brush connected to the interior side of a cap. The brush is immersed in the fluid when the cap is attached to the bottle. Upon removing the cap, the attached brush retains a small volume of fluid, which is applied to the desired surface by direct contact. Other direct-contact fluid applicators are known. For example, fluid may be dispensed by forcing it through a porous material that is permeable to the fluid, such as a sponge. Additionally, a porous and permeable dauber may be immersed within the fluid and used to apply the fluid to a surface, similarly to the above-described brush.

The preferred method of applying a fluid to a surface may depend on circumstances that are not known in advance. For example, a liquid skin bandage fluid having efficacy in treating poison ivy may be optimally applied to the skin in a generally even manner over a relatively large area in an atomized spray. However, the same fluid, which additionally has efficacy in treating cuts, scrapes, puncture wounds, and the like, may be optimally applied to a localized area of skin in a controlled manner by direct application, using a dauber or brush. While the fluid could be packaged and sold in both a container having a pump spray mechanism and also a container having a direct-application dauber or brush attached to the cap, this multiplicity of packaging complicates the manufacture, distribution, and sale of the fluid. Additionally, since customers do not know in advance which application method may be preferred, they must purchase the same fluid in both types of containers, increasing their cost and cluttering their storage areas.

SUMMARY

According to one or more embodiments of the present invention, fluid may be dispensed from a container in a filtered spray mode or a direct application mode. A porous and permeable filter covers the open end of a fluid feed to providing fluid to a pump spray mechanism. The filter protects the pump spray mechanism from becoming clogged with particulate matter that may be present in the container. Fluid may additionally be dispensed from the container by removing the pump spray mechanism from the container, and applying fluid retained in the filter directly to a surface.

One embodiment relates to a filtered fluid pump spray dispenser and applicator assembly. The assembly includes container having a base, body, and a bore opposite the base. The container is operative to hold a fluid to be dispensed. The assembly further includes a pump spray apparatus operative to extract fluid from the container and spray the fluid in an at least partially atomized form under manual actuation. A fluid feed tube extends into the container and connects at one end to the pump spray apparatus in fluid flow relationship. A filter covers a free end of the fluid feed tube. The filter is operative to filter particulate matter from fluid sprayed by actuation of the pump spray apparatus, and is further operative to retain and dispense fluid by contact with a surface when the fluid feed tube is removed from the container.

Another embodiment relates to a method of applying fluid to one or more surfaces from a container having a fluid feed tube interposed between a pump spray apparatus and a filter. In one mode, a pump spray apparatus is manually actuated so as to draw fluid from the container through the filter and fluid feed tube, at least partially atomize the fluid, and direct the resulting spray generally towards a surface. In another mode, the pump spray apparatus, fluid feed tube, and filter are removed, and fluid is applied to a surface in a controlled manner by direct contact of the filter to the surface.

DETAILED DESCRIPTION

Figure 1:
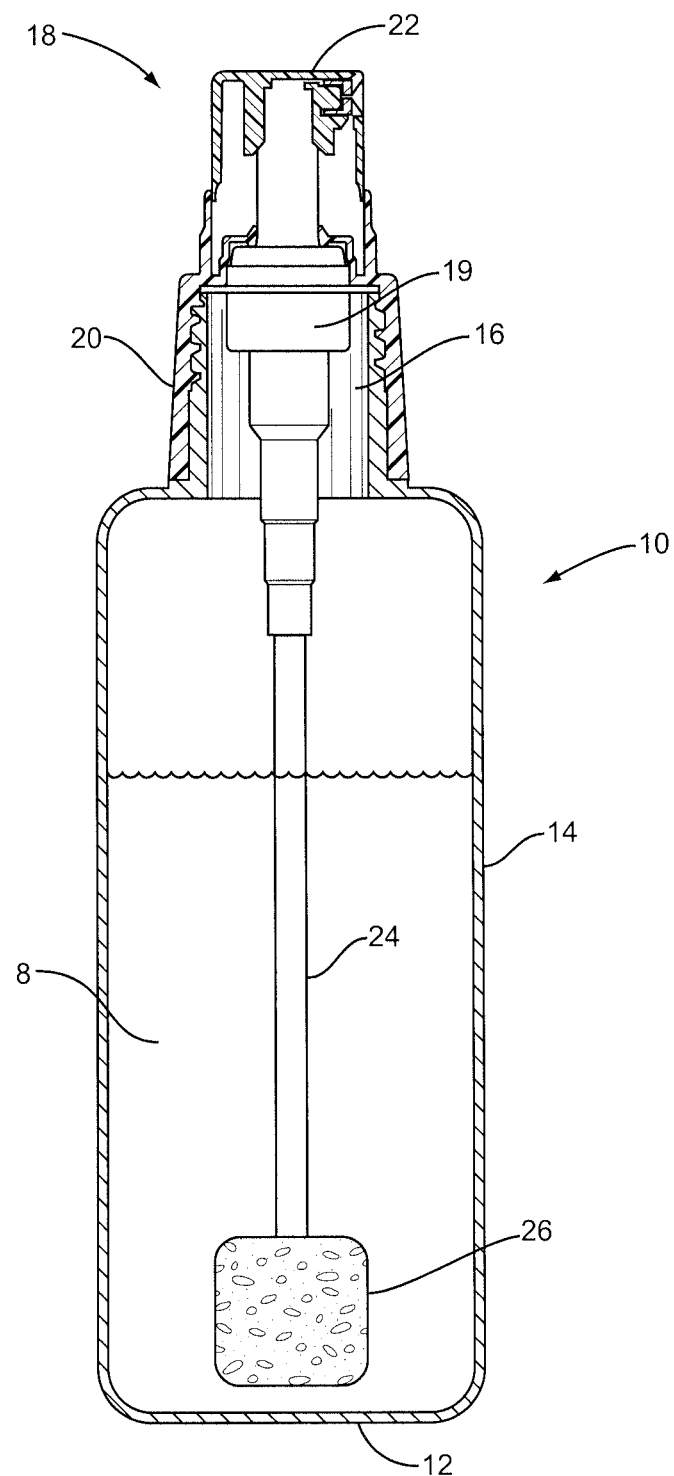
FIG. 1 is a section view of a filtered spray pump container according to one embodiment of the present invention.

FIG. 1 depicts a filtered fluid pump spray dispenser and applicator assembly according to one embodiment of the present invention. A container 10 includes a base 12, a body 14, and an externally threaded bore 16 opposite the base 12. Of course the container 10 may, in general, comprise any shape, size, or orientation, and may be formed of plastic, glass, fiberglass, waterproofed cardboard, or any other suitable material or combination of materials. The container holds a fluid 8 to be dispensed. In one embodiment, the container body 14 is transparent or translucent, or includes a transparent or translucent area (i.e., a window or sight glass, not shown) to monitor the level of fluid 8.

A pump/cap assembly 18 comprises a pump mechanism 19, a cap portion 20, and a pump actuator 22 that is moveable with respect to the cap portion 20. The pump/cap assembly 18 attaches to the bore 16 with internal threads of the cap portion 20. A fluid feed tube 24 is connected at one end to the pump 19, in fluid flow relationship, and is open at the opposite end, which is disposed in close proximity to the base 12 of the container. Prior to essentially all of the fluid 8 being dispensed from the container 10, the open end of the fluid feed tube 24 is immersed in the fluid 8 when the container 10 is in a generally upright position, as depicted in FIG. 1. A filter 26, formed of a porous material that is permeable to the fluid 8, is disposed over and surrounds the open end of the fluid feed tube 24.

Figure 2:
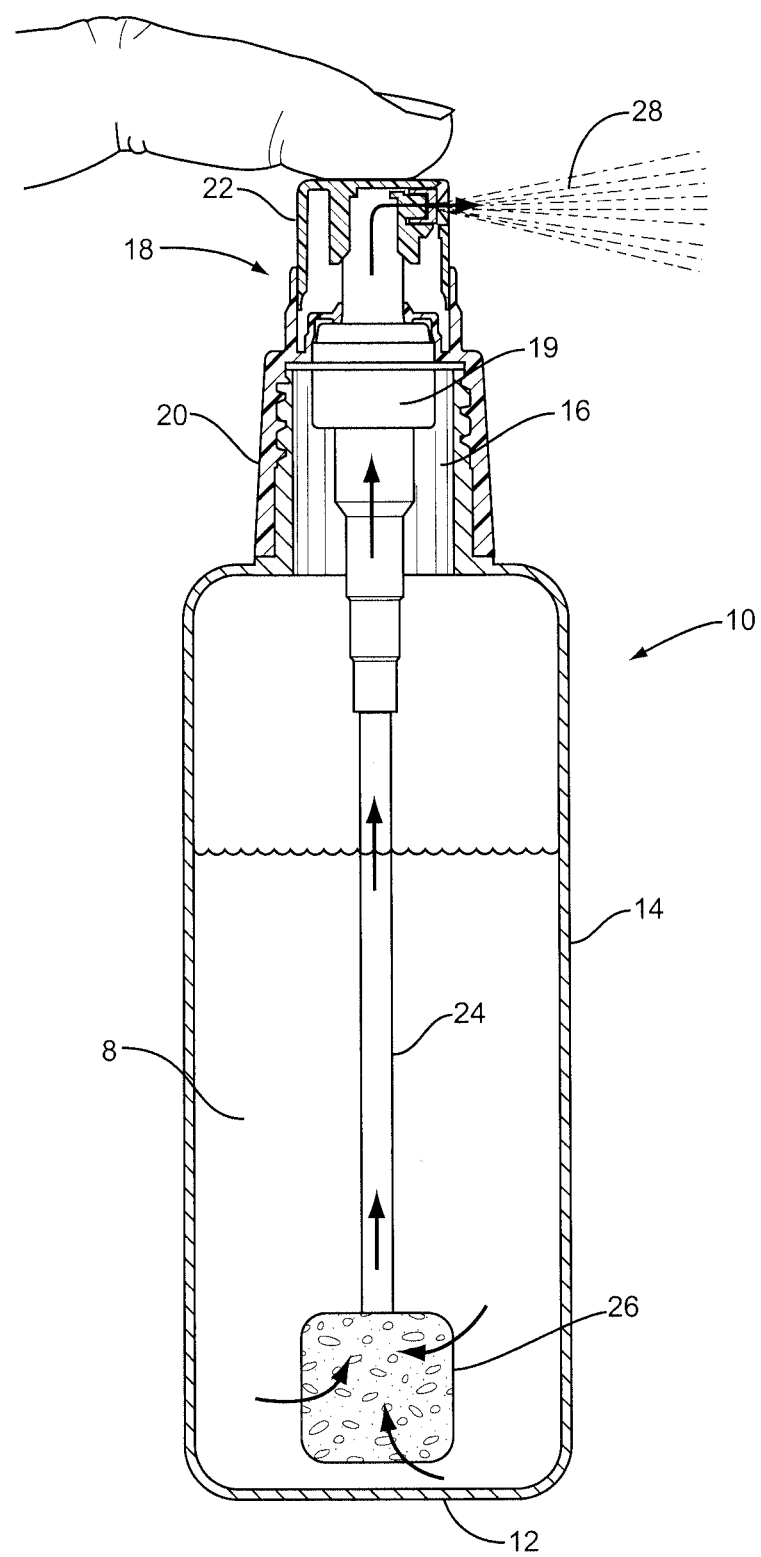
FIG. 2 is a section view of the container of FIG. 1 dispensing fluid in a spray mode.

FIG. 2 depicts the actuation of the pump 19, and the atomizing and spraying of fluid 8 from the container 10. As the pump actuator 22 is manually depressed, the pump 19 draws fluid 8 through the filter 26, into the fluid feed to 24, and through the pump/cap assembly 18. The pump/cap assembly 18 at least partially atomizes the fluid 8, and discharges it in a generally uniform spray 28. Numerous variations of the pump/cap assembly 18 are known in the art, any of which may be advantageously utilized in the present invention. The pump/cap assembly 18 depicted in FIGS. 1 and 2 is representative only, and is not limiting.

As depicted by fluid flow lines in FIG. 2, the fluid 8 must pass through the porous and permeable filter 26 prior to entering the fluid feed tube 24. Any particulate matter in the container 10, which may clog the tube 24 or pump 19, is trapped by the filter 26, and does not enter the fluid feed to 24. Such particulate matter may, without limitation, comprise dirt or other contaminants, or solids that may precipitate out the fluid 8 over time due to age, environmental conditions, or the like. The particulate matter may be suspended within the fluid 8, or may have settled to the base 12 of the container 10. In either case, the filter 26 traps the particulate matter, thus ensuring that the pump 19 is not impaired or rendered inoperative due to contamination. The filter 26 is thus an innovative advance in the state of the art of pump spray bottles. The filter 26 may be formed of any material that is permeable to the fluid 8 to be dispensed. For example, and without limitation, the filter 26 may be formed of a sponge material, cloth, or the like. The filter 26 may also comprise porous inner and outer sidewall members, with a fibrous material providing a filtering and fluid 8 retention functionality.

Figure 3:
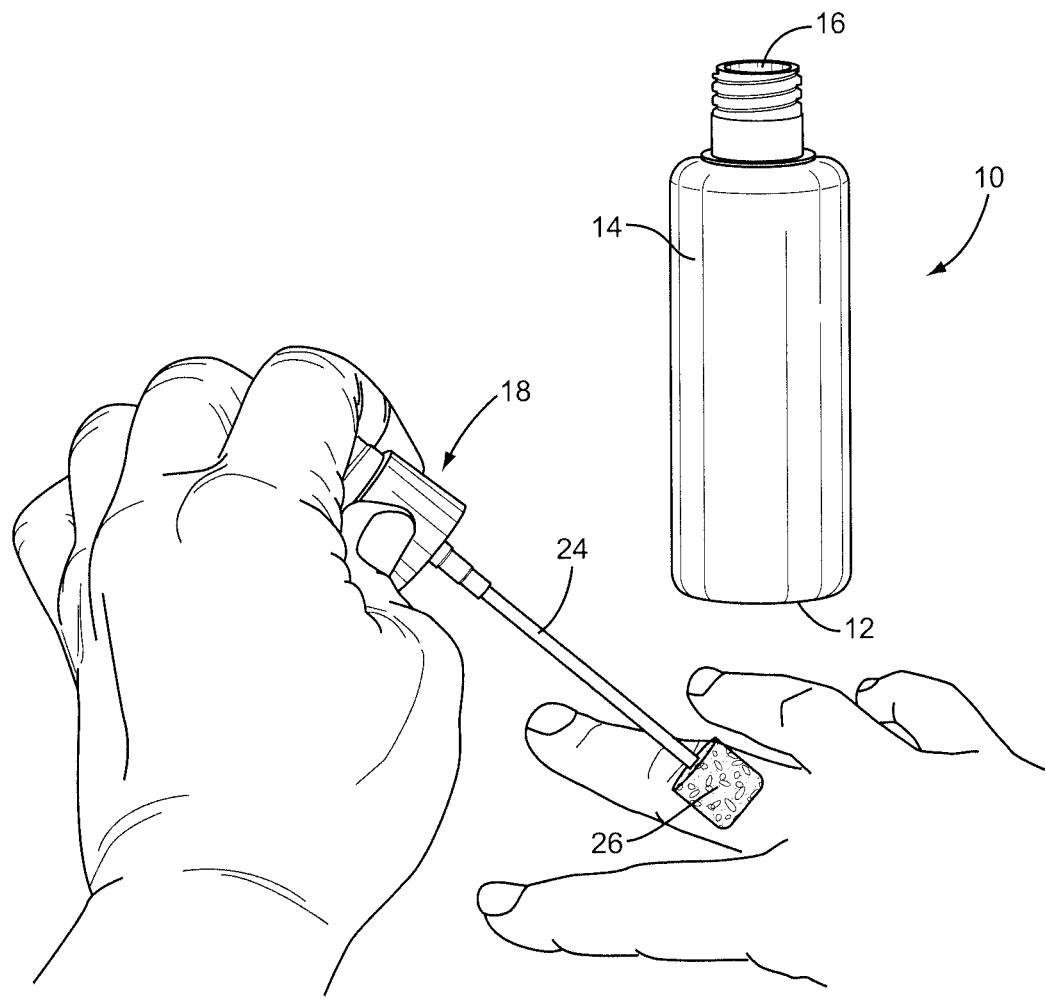
FIG. 3 is a perspective view of a user dispensing fluid from the container of FIG. 1 in a direct application mode.

Users do not always wish to dispense a fluid 8 from the bottle 10 in a spray. For example, the fluid 8 may comprise a liquid skin bandage, which a user may wish to apply to a cut or abrasion, and limit the application to a small area of skin. In this case, the pump/cap assembly 18 may be removed from the bottle 10, with the fluid feed tube 24, and hence the filter 26, attached. Due to the porosity of the filter 26, it retains a small amount of fluid 8, and due to its permeability to the fluid 8, it may act as a dauber to apply the fluid 8 to a small area of a surface, in a controlled manner, as depicted in FIG. 3. If fluid 8 has previously been dispensed from the bottle 10 via the pump 19, the fluid feed tube 24 will contain additional fluid 8, at least below the fluid 8 surface level. This additional fluid 8 will flow to the filter 26, as fluid 8 within the filter 26 is applied to a surface. Note that any dirt or contaminant picked up by the filter 26 from a surface, in direct application of fluid 8 to the surface, which may subsequently float freely within the fluid 9 in the container 10, is trapped by the filter 26 when the pump 19 is actuated, and thus does not clog the pumping mechanism. Further, in one embodiment, the filter 26 may be replaced with a new filter 26 if it becomes dirty, simply by removing the old filter 26 from the fluid flow tube 24 and attaching a new filter 26.

Fluid 8 may be dispensed from the container 10 either in spray form or direct application, as the user desires or requires. The two modes of fluid 8 application may be alternated or utilized in any order.

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. A method of applying fluid to one or more surfaces from a container having a fluid feed tube interposed between a pump spray apparatus and a filter, comprising:

manually actuating the pump spray apparatus so as to draw fluid from the container through the filter and fluid feed tube whereby the filter is operative to filter particulate matter from fluid, at least partially atomize the fluid, and direct the resulting spray generally towards a surface; and removing the pump spray apparatus, fluid feed tube, and filter, and applying fluid to a surface in a controlled manner by direct contact of the filter to the surface.

2. The method of claim 1 wherein applying fluid to a surface in a controlled manner by direct contact of the filter to the surface further comprises applying pressure to the filter against the surface.

3. The method of claim 1 further comprising dipping the filter back into the fluid in the container, and applying additional fluid to a surface in a controlled manner by direct contact of the filter to the surface.

4. The method of claim 1 further comprising removing the filter from the feed tube and replacing it with another filter.

5. The method of claim 1 wherein the fluid comprises a liquid skin bandage and at least one surface comprises epidermal tissue.

\* \* \* \* \*